(12) United States Patent
Irion et al.

(10) Patent No.: US 6,656,110 B1
(45) Date of Patent: Dec. 2, 2003

(54) ENDOSCOPIC SYSTEM

(75) Inventors: Klaus Irion, Liptingen (DE); Hartmut Wenzler, Frittlingen (DE); Peter Schwarz, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/403,148
(22) PCT Filed: Apr. 16, 1998
(86) PCT No.: PCT/EP98/02224

§ 371 (c)(1),
(2), (4) Date: Jan. 10, 2000

(87) PCT Pub. No.: WO98/46120

PCT Pub. Date: Oct. 22, 1998

(30) Foreign Application Priority Data

Apr. 16, 1997 (DE) .......................................... 197 15 951

(51) Int. Cl.⁷ .................................................. A61B 1/00
(52) U.S. Cl. ................. 600/117; 600/103; 600/109; 606/130; 348/75
(58) Field of Search ................... 600/102, 103, 600/114, 117, 118, 100, 160, 166, 170, 171, 417, 429; 348/45, 74; 606/130

(56) References Cited

U.S. PATENT DOCUMENTS

| | | | |
|---|---|---|---|
| 4,656,508 A | * | 4/1987 | Yokota ........................ 348/70 |
| 5,253,647 A | | 10/1993 | Takahashi et al. |
| 5,383,454 A | | 1/1995 | Bucholz |
| 5,417,210 A | | 5/1995 | Funda et al. |
| 5,503,320 A | | 4/1996 | Webster et al. |
| 5,704,897 A | | 1/1998 | Truppe |
| 5,800,179 A | * | 9/1998 | Bailey ........................ 434/262 |
| 5,957,833 A | * | 9/1999 | Shan ........................... 600/117 |

FOREIGN PATENT DOCUMENTS

| | | |
|---|---|---|
| EP | 0 495 351 B1 | 7/1992 |
| EP | 0 639 349 A2 | 2/1995 |
| EP | 0 672 389 A2 | 9/1995 |
| WO | WO 96/25881 | 8/1996 |
| WO | WO 97/19440 | 5/1997 |
| WO | WO 98/46120 | 10/1998 |

* cited by examiner

*Primary Examiner*—John Mulcahy
(74) *Attorney, Agent, or Firm*—St. Onge Steward Johnston & Reens LLC (57) ABSTRACT

An endoscope system includes position sensors which detect not only the position, but also the orientation, of both an endoscope (or endoscopes) and at least one instrument. The endoscope system includes an assessment and control unit which displays symbols which indicate, in addition to the position, the orientation of the instrument or instruments and possibly of the endoscopes relative to a displayed image.

67 Claims, 5 Drawing Sheets

ENDOSCOPIC SYSTEM

FIELD OF THE INVENTION

The present invention relates to an endoscopic system in accordance with the introductory clause of Patent claim 1.

The endoscopic systems of the claimed general type may be real systems for the application on the human or animal body or in the engineering field but they may also be simulation or training systems which a physician can use, for instance, for training endoscopic operations.

PRIOR ART

In minimal-invasive surgery (MIC) for instance surgical operations are performed with video assistance. When the endoscope or endoscopes is/are introduced together with the associated endoscopic camera system and the instrument or instruments, the physician does initially not dispose of the visual orientation of the instrument or instruments relative to the endoscope(s). This is true at least as long as the instruments are not visible in the coverage field of the endoscope or endoscopes.

But even when the physician sees the instrument with the endoscope he or she obtains only a two-dimensional image so that the information about the orientation of the instrument or the position of the distal end of the instrument relative to the focal plane, respectively, is initially missing.

A similar situation prevails with the endoscopic training or simulation systems mentioned already. Advanced systems merely comprise a housing which simulates the patient's body. Operating elements or handles, respectively, are mounted on the housing, which correspond to the proximal elements of the endoscopes or the handles of the instruments, respectively. The movements which the physician performs with the operating or control elements or handles, respectively, are detected by means of position sensors and supplied to a computer. The computer displays on a screen the movement of the distal functional elements, which do not exist in reality in advanced simulation systems, in an "apparently real" environment, i.e. the respective body cavity, for instance, with a simultaneous representation of organs and the process of their treatment, etc. In this manner it is possible to simulate the course of a real surgical operation on the screen in (almost) all details.

As a (presumed) solution to the aforementioned problem of lack of information about the orientation of the instruments endoscopic systems have been proposed in which the positions of the instruments are represented on a monitor:

An endoscopic system which the wording of the introductory clause of Patent claim 1 starts out from is known from the U.S. Patent U.S. Pat. No. 5,503,320. The system disclosed in that prior art reference comprises at least one endoscope the objective of which generates an image of the area to be subjected to diagnosis or a surgical operation.

This system is recorded by a video recorder and represented on a monitor. Moreover, at least one instruments such as a pair of scissors, an HF instrument, a clip applicator or the like is provided which is used to perform the treatment or diagnostic process proper. For a determination of the position of the instrument or instruments a position sensing means is provided. For the illustration of the position of the instrument or instruments symbols are displayed on the monitor which represent the positions of the instrument or instruments. The term "position" is to be understood here to denote the co-ordinates of a particular "point", as a rule the distal end of the respective instrument.

Similar systems are known from the European Patents EP 0 495 351 B1, EP 0 672 389 A2, the U.S. Patents U.S. Pat. No. 5,253,647, U.S. Pat. No. 5,383,454 and U.S. Pat. No. 5,417,210.

By the way, as far as the explanation of all terms not described here in details is concerned, as well as the implementation in engineering terms, i.e. the sensors, assessment and controller units used, etc., explicit reference is made to the aforementioned prior art documents.

In accordance with the present invention the applicant has become aware of the fact that the system known from the U.S. Pat. No. 5,503,320, which discloses the prior art of the claimed general type, entails the disadvantage that merely the position of the distal end is displayed, rather than the orientation of the instrument in space. As a result, it is difficult for the operator to determine the orientation of the instrument on the merely two-dimensional image. The orientation is, however, decisive for the manipulation of the instruments:

When the instrument is moved forward, for instance, the orientation determines the site which the instrument will "hit next".

BRIEF DESCRIPTION OF THE INVENTION

The present invention is therefore based on the problem of improving an endoscopic system according to the introductory clause of Patent claim 1 in such a way that the operator will be able to lead the instruments or instruments more rapidly into the field of vision of the endoscope, and that the operator will furthermore obtain information about the orientation of the instruments.

One inventive solution to this problem is defined in Patent claim 1. Improvements of the invention are the subject matters of the claims 2 et seq.

The invention starts out from an endoscopic system which comprises at least one endoscope the objective of which generates an image of the area to be observed, (at least) one video recorder which records the image of the objective of the endoscope, at least one instrument such as a pair of scissors, an HF instrument, a (technical) manipulator or the like, a position sensing means which detects the position of the instrument or instruments or the endoscope or endoscopes, respectively, and an assessment and control unit to which the output signal of the video recorder and of the position sensing means are applied and which displays an image of the operation field projected by the endoscope objective on a monitor, and furthermore symbols representing the position of the instrument (e.g. surgical instrument).

In accordance with the present invention this endoscopic system is improved by the provisions that the position sensing means comprises sensors which detect not only the position but also the orientation of both the endoscope(s) and the instrument(s), and that the displayed symbols reflect the orientation of the instrument or instruments and possibly of the further endoscopes relative to the displayed image. With endoscopes having a viewing direction which encloses an angle different from 0° relative to the longitudinal axis of the endoscope, i.e. so-called inclined-view endoscopes, it is, of course, also possible to fade in some information about their orientation. Moreover, it is also possible to display information about the orientation and particularly the rotational position of the instruments.

The endoscopic instrument set consisting of at least one endoscope with a video recorder system and at least one instrument is hence extended to the effect that each of the endoscope(s) and the instrument(s) comprises a position sensor which detects both the position and the direction or orientation of the instrument or the endoscope, respectively. The local information and the additional positional information are supplied to a processor unit which computes a so-called direction marker which is displayed in the video image on the monitor, preferably in the marginal image area of the endoscopic image or in an (additional) electronic frame which may be disposed around the tube in particular. As will be described-still below, the fading-in of the (local and) directional information is performed preferably on when the instruments are not in the field of vision of the endoscope. The directional marker at the margin of the endoscopic image on the monitor is coded in terms of position, direction, and/or spacing from a reference point, e.g. on the line of sight of the endoscope.

In parallel or possibly also as an alternative an acoustic guiding signal may be used as well.

In particular, the symbol represented by the assessment and control unit or the acoustic signal can indicate the direction of entry and the site of entry of the respective instrument into the recorded image. It is particularly preferable to have a symbol represented by the assessment and control unit, which reflects the specific site where the extension of the longitudinal axis of an instrument beyond the image or frame passes through the coverage field cone of the endoscope. This may be realised in particular by the provision that the symbol represented by the assessment and control unit indicates the particular azimuth angle and the direction at or in which the extension of the longitudinal axis of the instrument penetrates the coverage field cone.

The operator receives information about the orientation and the site of the respective instrument in a particularly practice-oriented manner by the fact that the assessment and control unit constructs a plane which is located ahead of the distal end of the endoscope at a definable distance, and that the assessment and control unit represents another symbol indicating the specific site where the extension of the longitudinal axis of the instrument penetrates this plane. As a result, the operator knows whether the instrument will be brought into engagement at the desired site with the tissue to be removed, for example.

This plane may be that plane in particular onto which the objective is focussed, i. e the plane of the image.

It is moreover preferred that the symbol represented by the assessment and control unit will indicate the distance between the distal end of the respective instrument and the image recorded by the objective.

In another embodiment of the invention the symbol indicates whether the axis of the associated instrument does or does not intersect with the coverage field cone of the objective.

In all the aforementioned cases it is moreover expedient that the respective indication is furnished by a different graphic coding of the symbol. The graphic coding may be performed, for instance, in the manner of a bar chart.

The sensors can detect, in particular, also the rotational position of the instruments and/or the endoscope. This is particularly important for so-called inclined-view endoscopes. The assessment and control unit then derives, from the output signal of the sensor associated with an endoscope, the orientation of the optical axis of the endoscope objective. The same applies by way of analogy to instruments performing manipulations which depend on the respective rotational position of the instrument.

In an improved embodiment of the invention the assessment and control unit superimposes the symbols onto the endoscope image on the monitor. It is particularly expedient when the assessment and control unit represents the symbols on the monitor outside the endoscope image proper. To this end a frame may be provided—as has been described above already—which surrounds the display area on the monitor, with the assessment and control unit representing the symbols on this frame. The frame may include light-emitting lighting elements such as miniature lamps or LEDs.

It is preferable in any case that the assessment and control logic represents a symbol only when the associated instrument is not visible in the endoscope image—as has been described above already—because in such a case the operator will not be strained with the representation of symbols which are, actually speaking, superfluous.

In the system proposed in accordance with the present invention the sensors may be mounted on the proximal or distal ends on the instruments or on the endoscope(s). The endoscope(s) or the instrument(s) may be rigid endoscopes or instruments or flexible endoscopes or instruments. In the case of flexible endoscopes or instruments, respectively, it is preferred that a sensor detects the respective bending.

The inventive system is not only suitable to generate an indication for an operator; in an improved embodiment the assessment and control unit may control a guiding system for the instrument(s). This guiding system may co-operate with the operator in a passive or an active manner, which means that the operator can receive hints as to the manipulation or positioning of instruments or intervene in the handling of the instruments.

It is possible that the guiding system allows for a movement of the distal end of the particular instrument into the endoscope image only, inter alia when the distal end of the instrument or instruments is located beyond the endoscope image. In particular, the guiding system may allow for a manipulation of the respective instrument only when the distal end of this instrument is located in the endoscope image. To this end, the instruments may include a marker which is optically detected by the assessment and control unit by means of the endoscope or endoscopes, respectively, and which serves as point of reference for the guiding system.

On principle, any endoscopes may be employed as endoscope, e.g. conventional rigid or flexible endoscopes on which video units are flange-mounted on the eyepiece funnel. Furthermore, endoscopes may be used where the image recorder of the video unit is disposed on the distal end. The application of stereo endoscopes is particularly preferred which record stereo images. With such endoscopes it is possible that the assessment and control unit defines, by triangulation, the position of a specific point in the endoscope image and selects this point as reference point for the guiding system. In such a case it is preferred that the monitor is a stereo display on which the symbols are displayed in a three-dimensional representation. These three-dimensional symbols may also indicate the point of penetration and the direction of penetration of the respective instrument.

For measuring and hence for a quantitative evaluation moreover a projector means may be provided which projects a two-dimensional pattern onto the area to be subjected to diagnosis or a surgical operation. The assessment and control unit reconstructs then the topography of the area on the basis of the image of the two-dimensional pattern. This pattern may be a network or a dot matrix.

BRIEF DESCRIPTION OF THE DRAWING

The invention will be described by one exemplary embodiment in the following, without any restriction of the general inventive idea, with reference to the drawing which is explicitly referred to in all other respects as far as the disclosure of all inventive details is concerned which are not fully explained in the text. In the drawing.

DESCRIPTION OF AN EMBODIMENT

In FIGS. 1 to 4 the reference numeral 1 denotes an endoscope which, in the illustrated embodiment, is a rigid endoscope, without any restriction of the general inventive idea. An endoscope objective, which is not illustrated in more details, is disposed on the distal end 11 of the endoscope 1. The reference numeral 2 indicates the plane(image plane) onto which the endoscope objective is focused, whilst the numeral 21 denotes the a associated coverage field cone of the endoscope objective.

Without any restriction of the general inventive idea, the endoscope 1 in the illustrated embodiment comprises a non-illustrated known relay lens system which transmits the image recorded by the endoscope objective to the proximal end of the endoscope 1. A video unit 3, which is flange-mounted on the eyepiece funnel of the endoscope 1, records the image from the eyepiece so that it may be displayed as image 2' on the monitor 4. Moreover, the reference numeral 5 denotes an instrument which serves to perform an operation such as a diagnosis or a therapeutical treatment.

In accordance with the invention, a position-sensing means is provided which is not illustrated in more details and which comprises sensors detecting the position and the orientation of the instrument 5 relative to the image plane 2 as well as to the coverage field cone 21 of the endoscope 1. These sensors may be disposed on the distal or proximal end. The output signal from the sensors is applied to an assessment and control unit, which is not represented either and which may comprise in particular a video processor unit.

The position and the orientation of the instrument are represented by symbols which are superimposed by the assessment and control unit, which is not illustrated in further details and comprises, for instance, a PC or a workstation, onto the endoscope image 2' on the monitor 4, or which are displayed on the side of this display.

In the illustrated embodiment the assessment and control unit displays, however, the symbols on the monitor 4 outside the actual endoscope image 2' proper.

Figure 1:
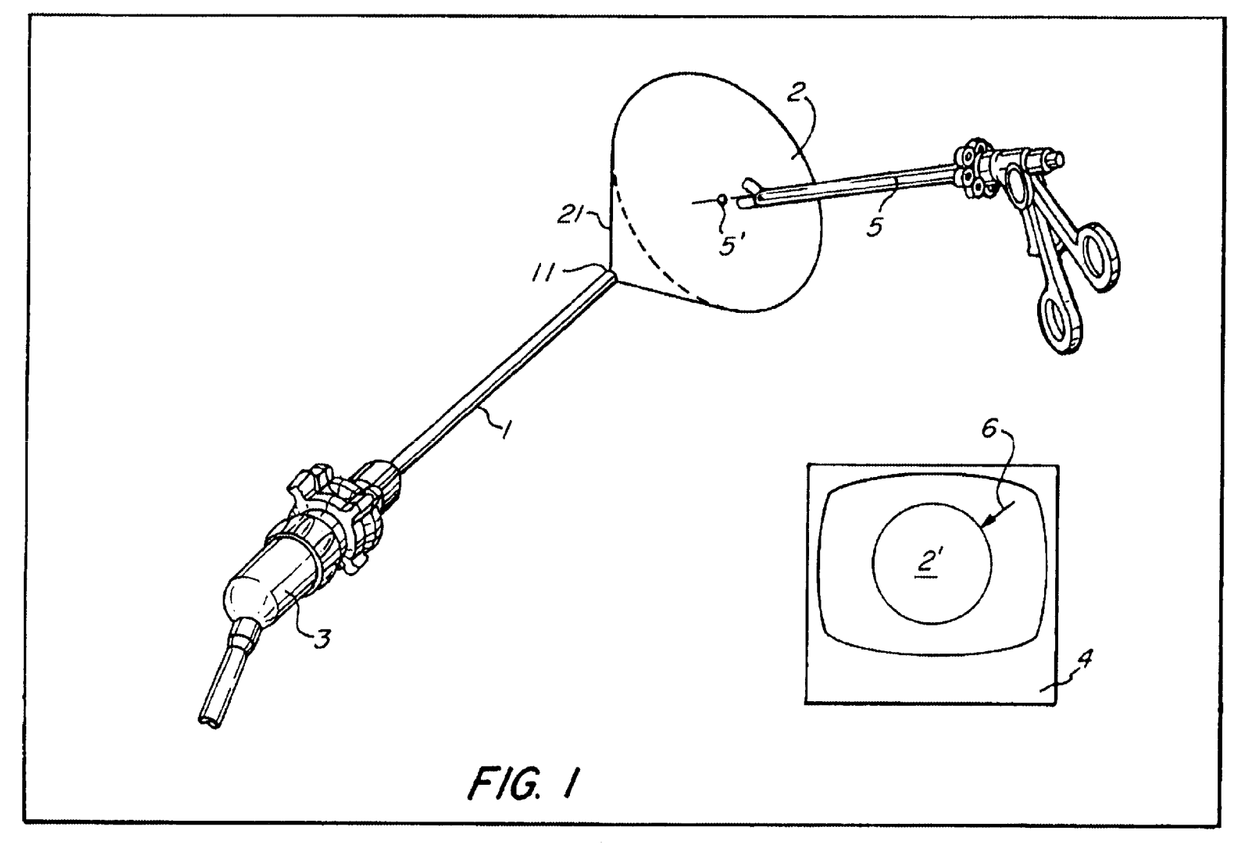
FIGS. 1 to 5 illustrate different arrangements of an instrument in the coverage field of an endoscope and the associated symbols displayed on a monitor.

In FIGS. 1 to 4 examples of symbols are illustrated (arrows 6, 6' and 6") which indicate the orientation of the instrument 5 relative to the coverage field 2. This will be explained in the following:

FIG. 1 shows the case that the instrument 5 has not yet entered the coverage field cone 21 of the objective. The longitudinal axis of the instrument 5 is, however, oriented in such a direction that the instrument 5 will enter the coverage field cone 21 when its advance movement is continued.

This is symbolically displayed by the arrow 6 on the monitor 4, which points at the coverage field 2 of the endoscope 1. The reference numeral 5' denotes the point at which the extension of the longitudinal axis of the instrument 5 penetrates the image plane 2.

Figure 2:
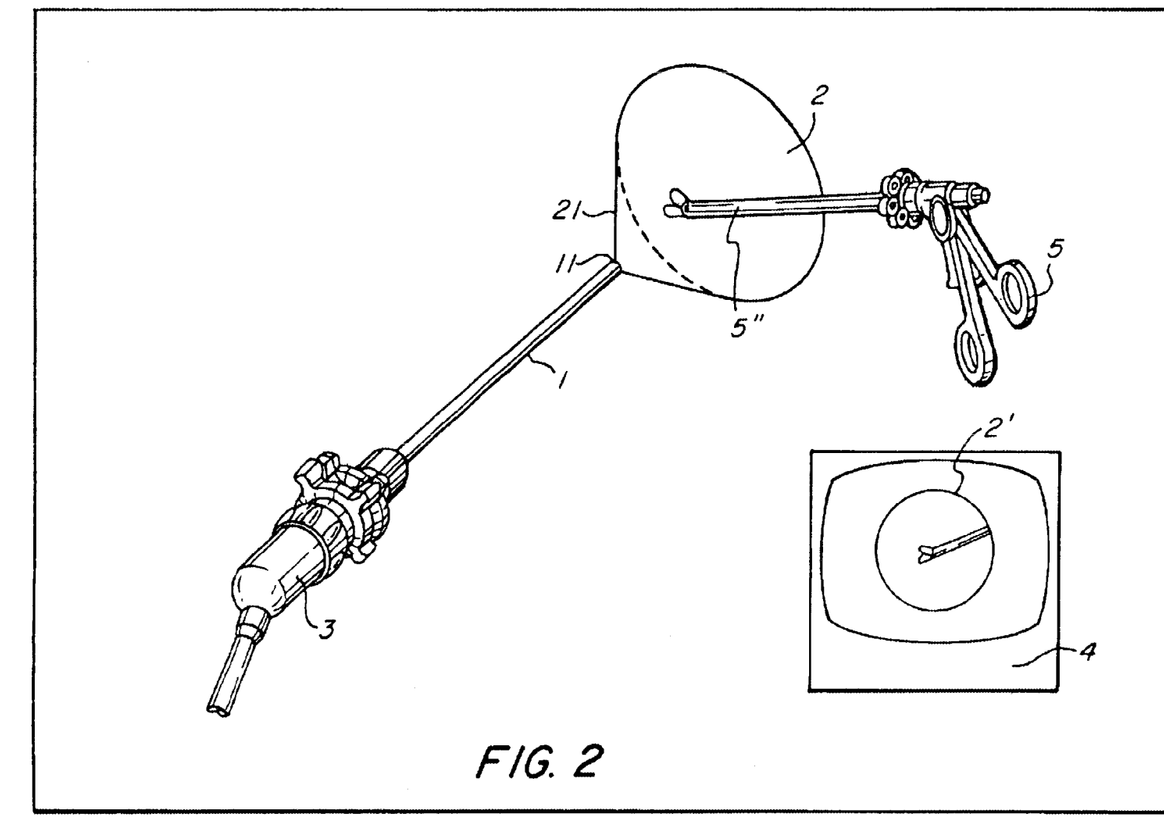

FIG. 2 illustrates the case where the distal end of the instrument 5 is located in the coverage field cone 21. As the operator sees the distal end of the instrument 5 on the monitor 4 a representation of a symbol indicating the position and the orientation of the instrument 5 is dispensed with so as to avoid confusion on the operator's part.

However, in order to signal the three-dimensional association of the instrument 5 relative to the image plane 2 to the operator, the point of penetration 5" of the instrument 5 through the image plane 2 may be displayed.

Figure 3:
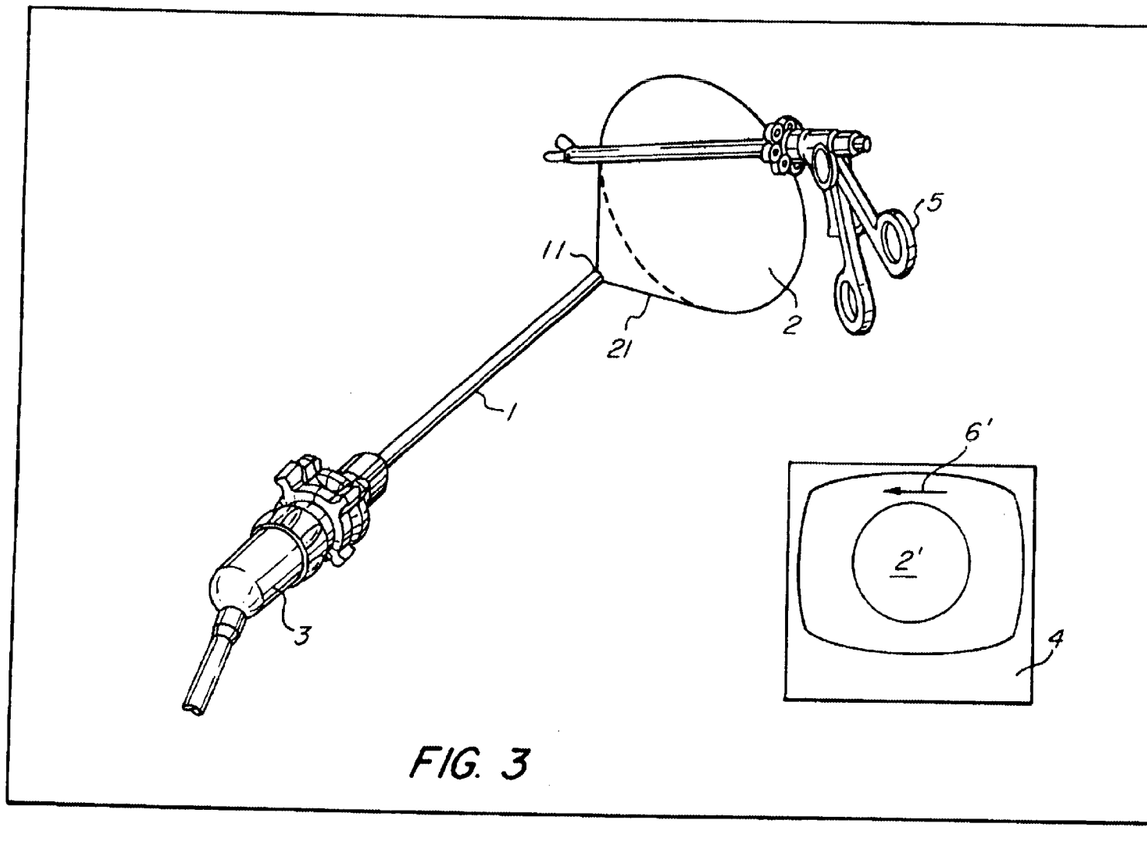

FIG. 3 is a representation of the case where the instrument 5 is located ahead of the distal end 11 of the endoscope but where it is so disposed and oriented that the extension of the longitudinal axis of the instrument 5 will not intersect the coverage field cone 21; the instrument 5 is rather disposed "above the coverage field cone 21".

This arrangement and such orientation is symbolically indicated by an arrow which is displayed on the monitor above the image 2' with an extension which symbolises the position and the orientation of the instrument 5.

Figure 4:
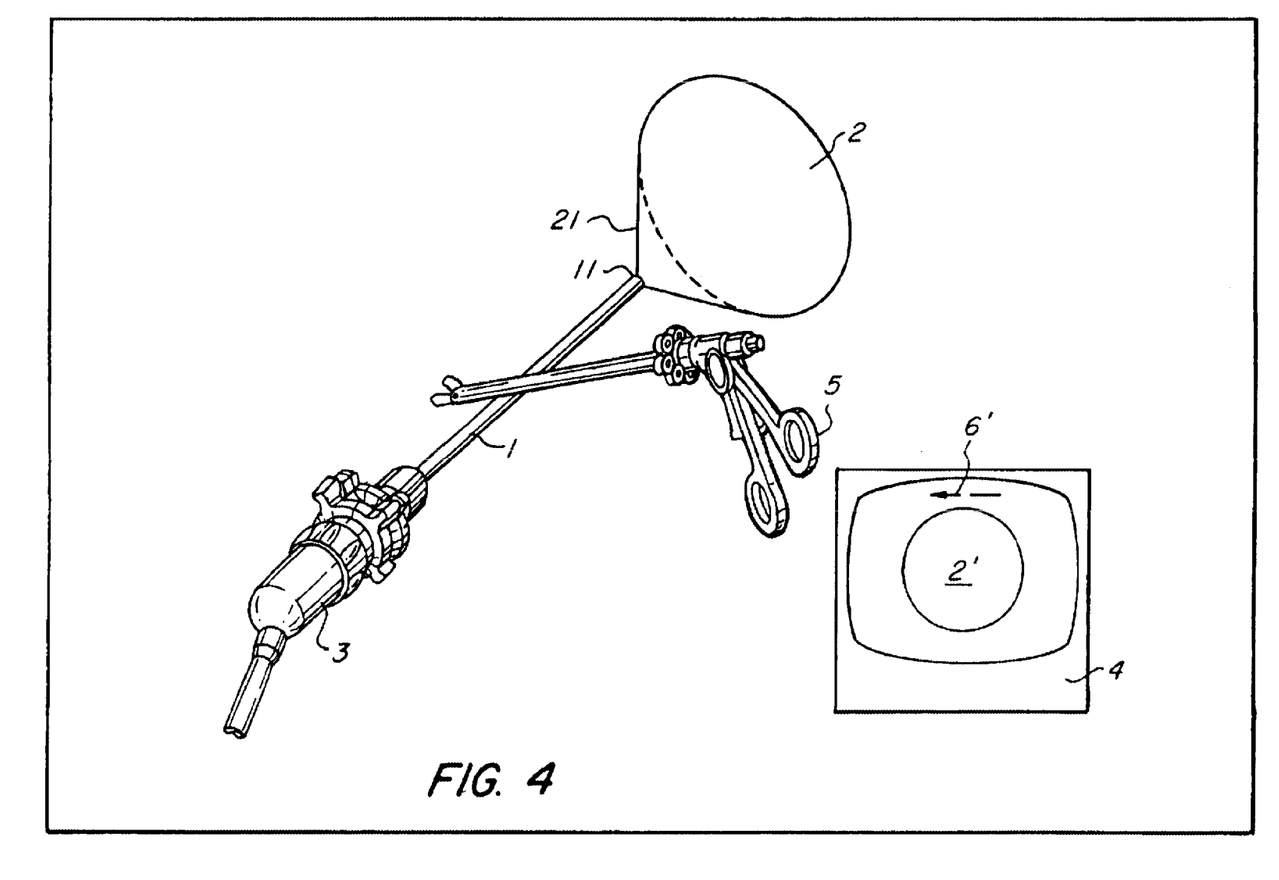

FIG. 4 illustrates the case where the instrument 5 is located along the viewing direction ahead of the distal end 11 of the endoscope 1 whilst it is so oriented that the instrument cannot intersect the coverage field cone 21 when its advance movement is continued.

In the illustrated embodiment this orientation is symbolically indicated by an interrupted arrow 6".

Figure 5:
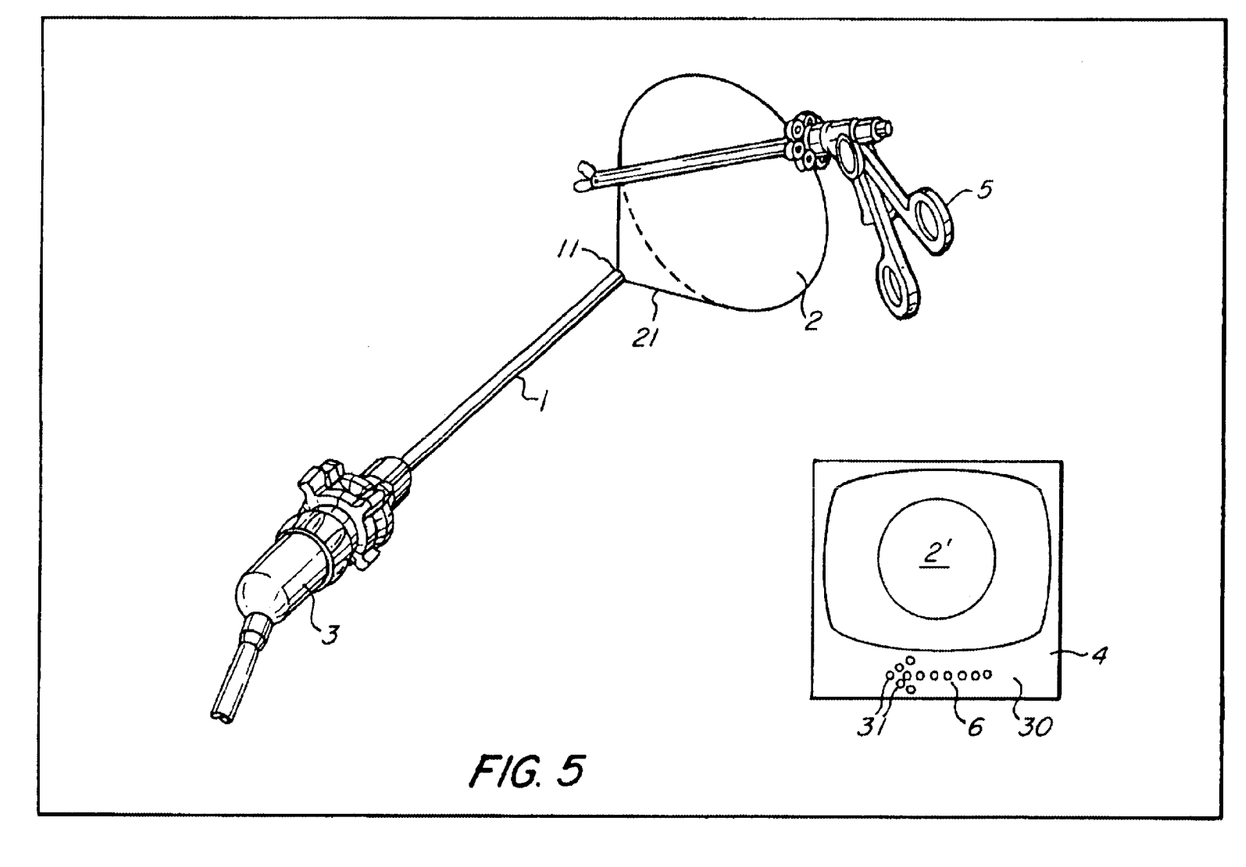

As shown in FIG. 5, a frame 30 may be provided—as has been described above already—which surrounds the display area of the monitor 4, with the assessment and control unit representing the symbols 6, 6', 6" on this frame 30. The frame 30 may include light-emitting lighting elements 31 such as miniature lamps or LEDs.

The invention has been described in the foregoing with reference to an embodiment. The most different modifications are, of course, possible:

It is possible, for instance, to use several endoscopes and/or instruments instead of one endoscope 1 and one instrument 5, with the position and orientation of these endoscopes and/or instruments being possibly displayed relative to one or several selected endoscopes and their coverage fields on one or several monitors.

It is moreover possible to use symbols—either as replacement of or additionally to arrows as graphic symbols—in which further information is coded. This information coding may be realised, for instance, in the manner of bar charts, by the colour of the symbols, or the like.

Furthermore, symbols indicating additional information may be displayed in addition to symbols such as arrows or the like which represent the position and/or the orientation. These symbols may be superimposed onto the endoscope image 2 or displayed outside the endoscope image 2 on the monitor 4 or outside the monitor proper, e. g. on the peripheral margin of the monitor image.

Additionally or as an alternative acoustic signals may also be used.

The positional information obtained in accordance with the invention can moreover be used also as input signals for guiding systems or the like.

INDUSTRIAL APPLICABILITY

The inventive endoscopic system is suitable for application in the field of medicine or engineering endoscopy in endoscopic operations of any kind, endoscopic diagnostic or treatment operations, or in endoscopic simulation or training equipment.

What is claimed is:

1. Endoscopic system comprising:
   at least one endoscope having an objective which generates an image of an area to be observed,
   at least one video recorder which records the image generated by said objective, at least one instrument, a position-sensing device which detects a position of the at least one instruments, and an assessment and control unit to which an output signal of the video recorder and the position-sensing device are applied and which displays on a monitor the image and symbols representing the position of the instrument, characterized in that said position-sensing device comprises a sensor which also detects orientation of the instrument, and that said assessment and control unit displays symbols which indicate, in addition to the position the orientation of the instrument, and characterized in that a frame is provided which surrounds the display surface of said monitor, and that said assessment and control unit displays the symbols on this frame.

2. Device according to claim 1, characterized in that said symbols or symbols displayed by said assessment and control unit indicate a direction of entry and a site of entry of the instrument into the recorded image.

3. System according to claim 2, characterized in that said assessment and control unit displays at least the symbols for a direction of entry and a site of entry into a coverage field cone only when the instrument is not visible in the endoscope image.

4. System according to claim 1, characterized in that said assessment and control unit displays at least one symbol indicating a specific site where an extension of a longitudinal axis of an instrument not inside the coverage field penetrates a coverage field cone of the endoscope.

5. System according to claim 4, characterized in that said symbol displayed by said assessment and control unit indicates a respective azimuth angle and direction at which an extension of a longitudinal axis of said instrument penetrates the coverage field cone.

6. System according claim 1, characterized in that said assessment and control unit computes a plane which is located at a definable distance ahead of a distal end of said endoscope, and that said assessment and control unit displays at least one further symbol indicating a site where an extension of a longitudinal axis of the instrument penetrates this plane.

7. System according to claim 6, characterised in that the plane is that plane onto which the objective is focused.

8. System according to claim 6, characterized in that said assessment and control unit displays the symbol indicating a point of penetration through a plane only when a distal end of the instrument, along a viewing direction, is located in front of the plane so that the instrument will not penetrate the plane.

9. System according to claim 1, characterized in that the symbol displayed by said assessment and control unit indicates a distance between a distal end of the instrument and the image recorded by said objective.

10. System according to claim 5, characterised in that the symbol is designed in the manner of a luminous bar display element.

11. System according to claim 5, characterized in that respective information is provided by a different graphic coding of the symbol.

12. System according to claim 1, characterized in that one of the symbols indicates whether an axis of the associated instrument intersects or does not intersect a coverage field cone of the objective.

13. System according to claim 1, characterized in that said sensors detect also a rotational position of the instrument.

14. System according to claim 1, characterized in that said assessment and control unit determines an orientation of an optical axis of the objective of the endoscope by deriving it from the output signal of a sensor associated with the endoscope.

15. System according to claim 14, characterized in that information about a viewing direction and a coverage field angle of the endoscope is applied to said assessment and control unit.

16. System according to claim 1, characterised in that said frame comprises light-emitting luminous elements such as miniature lamps or LEDs.

17. System according to claim 1, characterized in that said sensors are mounted on a proximal end on the instrument.

18. System according to claim 17, characterised in that said endoscope is a rigid endoscope.

19. System according to claim 17, characterized in that if the endoscope comprises a flexible endoscope an additional sensor is provided which detects a bend of said endoscope.

20. System according to claim 1, characterized in that said sensors are mounted on the distal end of said instrument.

21. System according to claim 1, characterized in that said assessment and control unit controls a guiding system for said instrument.

22. System according to claim 21, characterized in that said guiding system allows for a movement of a distal end of said instrument into the endoscope image when the distal end of said instrument is located outside the endoscope image.

23. System according to claim 21, characterized in that said guiding system allows for an operation of a respective instrument only when its distal end is located in said endoscope image.

24. System according to claim 21, characterized in that the instrument is provided with a mark which is optically detected by said assessment and control unit and which serves as point of reference for said guiding system.

25. System according to claim 21, characterized in that said assessment and control unit determines a position of a particular point in the endoscope image by means of triangulation, and selects this point as point of reference for said guiding system.

26. System according to claim 1, characterized in that said endoscope is a stereo endoscope.

27. System according to claim 26, characterized in that the monitor is a stereo display on which said symbols are displayed in a three-dimensional representation.

28. System according to claim 27, characterized in that said three-dimensional symbols indicate a point of penetration and a direction of penetration of the respective instrument.

29. System according to claim 1, characterized in that a projection means is provided which projects a two-dimensional pattern onto the area to be observed, and that said assessment and control unit reconstructs a topography of this area from the image of said two-dimensional pattern.

30. System according to claim 29, characterised in that said pattern is a network or a dot matrix.

31. System according to claim 1, characterized in that if the endoscope comprises an imaging inclined-view endoscope information is displayed concerning the angle between the longitudinal axis of the endoscope and the direction of viewing.

32. Application of a system according to claim 1 for the performance of endoscopic operations on the human or animal body.

33. Application of a system according to claim 1 in an endoscopic simulation or training system.

34. Application according to claim 33, characterized in that said endoscopic simulation or training system comprises a housing representing the human or animal body, as well as parts simulating proximal control elements, and that an image processor unit is provided which displays the distal functional elements on a monitor.

35. Endoscopic system comprising:
at least one endoscope having an objective which generates an image of an area to be observed,
at least one video recorder which records the image generated by said objective,
at least one instrument,
a position-sensing device which detects a position of the at least one instruments, and
an assessment and control unit to which an output signal of the video recorder and the position-sensing device are applied and which displays on a monitor the image and symbols representing the position of the instrument,
characterized in that said position-sensing device comprises a sensor which also detects orientation of the instrument, and that said assessment and control unit displays symbols which indicate, in addition to the position the orientation of the instrument,
characterized in that said assessment and control unit controls a guiding system for said instrument, and
characterized in that said guiding system allows for an operation of a respective instrument only when its distal end is located in said endoscope image.

36. Device according to claim 35, characterized in that said symbols or symbols displayed by said assessment and control unit indicate a direction of entry and a site of entry of the instrument into the recorded image.

37. System according to claim 36, characterized in that said assessment and control unit displays at least the symbols for a direction of entry and a site of entry into a coverage field cone only when the instrument is not visible in the endoscope image.

38. System according to claim 35, characterized in that said assessment and control unit displays at least one symbol indicating a specific site where an extension of a longitudinal axis of an instrument not inside the coverage field penetrates a coverage field cone of the endoscope.

39. System according to claim 38, characterized in that said symbol displayed by said assessment and control unit indicates a respective azimuth angle and direction at which an extension of a longitudinal axis of said instrument penetrates the coverage field cone.

40. System according claim 35, characterized in that said assessment and control unit computes a plane which is located at a definable distance ahead of a distal end of said endoscope, and that said assessment and control unit displays at least one further symbol indicating a site where an extension of a longitudinal axis of the instrument penetrates this plane.

41. System according to claim 40, characterized in that the plane is the plane on which the lens is focused.

42. System according to claim 35, characterized in that the symbol displayed by said assessment and control unit indicates a distance between a distal end of the instrument and the image recorded by said objective.

43. System according to claim 42, characterized in that the symbol takes the form of an illuminated bar display.

44. System according to claim 35, characterized in that one of the symbols indicates whether an axis of the associated instrument intersects or does not intersect a coverage field cone of the objective.

45. System according to claim 42, characterized in that respective information is provided by a different graphic coding of the symbol.

46. System according to claim 35, characterized in that said sensors detect also a rotational position of the instrument.

47. System according to claim 35, characterized in that said assessment and control unit determines an orientation of an optical axis of the objective of the endoscope by deriving it from the output signal of a sensor associated with the endoscope.

48. System according to claim 47, characterized in that information about a viewing direction and a coverage field angle of the endoscope is applied to said assessment and control unit.

49. System according to claim 35, characterized in that a frame is designed which surrounds the display window of the monitor and that the evaluation and control device presents the symbols on this frame.

50. System according to claim 49, characterized in that the frame has light-emitting illuminated elements such as miniature lamps or light diodes.

51. System according to claim 40, characterized in that said assessment and control unit displays the symbol indicating a point of penetration through a plane only when a distal end of the instrument, along a viewing direction, is located in front of the plane so that the instrument will not penetrate the plane.

52. System according to claim 35, characterized in that said sensors are mounted on a proximal end on the instrument.

53. System according to claim 52, characterized in that the endoscope is a rigid endoscope.

54. System according to claim 52, characterized in that if the endoscope comprises a flexible endoscope an additional sensor is provided which detects a bend of said endoscope.

55. System according to claim 35, characterized in that said sensors are mounted on the distal end of said instrument.

56. System according to claim 35, characterized in that said guiding system allows for a movement of a distal end of said instrument into the endoscope image when the distal end of said instrument is located outside the endoscope image.

57. System according to claim 35, characterized in that the instrument is provided with a mark which is optically detected by said assessment and control unit and which serves as point of reference for said guiding system.

58. System according to claim 35, characterized in that said endoscope is a stereo endoscope.

59. System according to claim 58, characterized in that the monitor is a stereo display on which said symbols are displayed in a three-dimensional representation.

60. System according to claim 59, characterized in that said three-dimensional symbols indicate a point of penetration and a direction of penetration of the respective instrument.

61. System according to claim 35, characterized in that said assessment and control unit determines a position of a particular point in the endoscope image by means of triangulation, and selects this point as point of reference for said guiding system.

62. System according to claim 35, characterized in that a projection means is provided which projects a two-dimensional pattern onto the area to be observed, and that said assessment and control unit reconstructs a topography of this area from the image of said two-dimensional pattern.

63. System according to claim 62, characterized in that the model is a network or a dot-halftone.

64. System according to claim 35, characterized in that if the endoscope comprises an imaging inclined-view endoscope information is displayed concerning the angle between the longitudinal axis of the endoscope and the direction of viewing.

65. Application of a system according to claim 35, for the performance of endoscopic operations on the human or animal body.

66. Application of a system according to claim 35, in an endoscopic simulation or training system.

67. Application according to claim 66, characterized in that said endoscopic simulation or training system comprises a housing representing the human or animal body, as well as parts simulating proximal control elements, and that an image processor unit is provided which displays the distal functional elements on a monitor.

* * * * *